United States Patent
Li et al.

(10) Patent No.: US 12,391,731 B2
(45) Date of Patent: Aug. 19, 2025

(54) METHOD FOR MODIFYING GLIADIN AND APPLICATION THEREOF

(71) Applicant: China Agricultural University, Beijing (CN)

(72) Inventors: Yixuan Li, Beijing (CN); Pengjie Wang, Beijing (CN); Genna Ba, Beijing (CN); Fazheng Ren, Beijing (CN); Siyuan Liu, Beijing (CN); Ran Wang, Beijing (CN); Longjiao Zhu, Beijing (CN); Rong Liu, Beijing (CN); Bing Fang, Beijing (CN); Ju Qiu, Beijing (CN); Xiaoyu Wang, Beijing (CN); Juan Chen, Beijing (CN); Han Chen, Beijing (CN); Yinhua Zhu, Beijing (CN); Chong Chen, Beijing (CN); Weibo Zhang, Beijing (CN); Xifan Wang, Beijing (CN); Jingjing He, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 18/412,625

(22) Filed: Jan. 15, 2024

(65) Prior Publication Data
US 2025/0074953 A1    Mar. 6, 2025

(30) Foreign Application Priority Data
Sep. 5, 2023 (CN) .......................... 202311132654.5

(51) Int. Cl.
*C07K 14/415* (2006.01)
*C07K 1/02* (2006.01)
*C12N 9/50* (2006.01)

(52) U.S. Cl.
CPC .............. *C07K 14/415* (2013.01); *C07K 1/02* (2013.01); *C12N 9/50* (2013.01); *C12Y 304/21026* (2013.01)

(58) Field of Classification Search
CPC ........... C07K 14/415; C07K 1/02; C12N 9/50
See application file for complete search history.

(56) References Cited

U.S. PATENT DOCUMENTS

2009/0081329 A1*   3/2009   Van Dijk ................. A23C 3/02
                                                            426/582

FOREIGN PATENT DOCUMENTS

| CN | 108938598 A | 12/2018 | |
| CN | 109259035 A | 1/2019 | |
| CN | 113208105 A | 8/2021 | |
| CN | 114699333 A | 7/2022 | |
| WO | WO-2017128556 A1 * | 8/2017 | .............. A23J 1/005 |

OTHER PUBLICATIONS

Translation of Liu_WO2017/128556 (Year: 2017).*
Jiang et al., "A pH shift approach to the improvement of interfacial properties of plant seed proteins", 2018, Current Opinion in Food Science, vol. 19, pp. 50-56 (Year: 2018).*
Mannheim et al., "Water-Soluble Zein by Enzymatic Modification in Organic Solvents", 1993, Cereal Chem., vol. 70, No. 2, pp. 115-121 (Year: 1993).*
Schober et al., "Impact of different isolation procedures on the functionality of zein and kafrinin", 2011, Journal of Cereal Science, vol. 54, pp. 241-249 (Year: 2011).*
Herold, N., "How Water Purity Impacts the Food and Beverage Industry", 2022, MECO, https://www.meco.com/how-water-purity-impacts-the-food-and-beverage-industry/ (Year: 2022).*
Fengyun Cao, Functions and Properties of Food Proteins, Applied Chemistry in Food, 2013, pp. 120-125, Agricultural University Press.

* cited by examiner

*Primary Examiner* — Nikki H. Dees
*Assistant Examiner* — Kelly P Kershaw

(57) ABSTRACT

A method for modifying a gliadin and an application thereof are provided. The method includes the following steps: dissolving the gliadin in a solvent to obtain gliadin solution; and adding a proline endoprotease to the gliadin solution for a reaction, and adjusting the pH value of solution to neutral according to a gradient, to obtain a modified gliadin. The modified gliadin obtained by the present invention may be uniformly dispersed in water, and may still maintain a uniform dispersion state in the water after high-temperature thermal sterilization and long-term storage, or even in the presence of sodium chloride, it has good thermal stability, salt resistance, and storage stability.

5 Claims, 4 Drawing Sheets

METHOD FOR MODIFYING GLIADIN AND APPLICATION THEREOF

CROSS REFERENCE TO THE RELATED APPLICATIONS

This application is based upon and claims priority to Chinese Patent Application No. 202311132654.5, filed on Sep. 5, 2023, the entire contents of which are incorporated herein by reference.

TECHNICAL FIELD

The present invention belongs to the technical field of gliadins and specifically relates to a method for modifying a gliadin and an application thereof.

BACKGROUND

Gliadins are one of components of plant seed storage proteins, and may be divided into a corn gliadin, a wheat gliadin and the like according to the source of raw materials; and according to the structure and solubility, it may be divided into a α-gliadin, a β-gliadin, a γ-gliadin and a δ-gliadin and the like. The gliadin has the unique solubility, it is insoluble in water or anhydrous alcohols, but may be dissolved in 60%-95% of alcohol or ketone aqueous solution. The gliadin is commonly used as a carrier for hydrophobic drugs or other functional components, as to prepare a related functional component delivery product, and it is widely used in pharmaceuticals, functional foods, and its derivative industries.

However, the biggest challenge currently limiting applications of the gliadin is its poor dispersibility in water. Under the conditions of thermal sterilization, long-term storage, or presence of various ions (such as sodium chloride), the gliadin is prone to aggregation and precipitation, and its applications are seriously limited by the above problems.

Solution methods in existing technologies are usually to compound the gliadin with high-molecular materials (such as a polysaccharide, a protein, and a chemically synthesized high polymer), so that a hydrophilic housing is formed on the surface of the gliadin, thereby the aggregation or precipitation of the gliadin is avoided. For example, patent document CN113208105A discloses a method for improving stability of a gliadin particle. This method reacts an MTGase catalytic cross-linked sodium caseinate with the gliadin, gliadin-cross-linked sodium caseinate composite nanoparticles obtained may serve as a delivery carrier for food active components, have slow-release properties and may improve the solubility and stability and the like of the food active components. However, the operation process of this method is complex, and the requirements for the compounding conditions of the gliadin and high molecules (including the mass ratio, compounding temperature, potential of hydrogen (pH), stirring rate of solution during compounding and the like) are extremely high. It is difficult to achieve uniform dispersion of all gliadin particles in a system, and introduction of a large number of other components in the compounding significantly weakens the functions of the gliadin particles, for example, the release performances of drugs in the body are often greatly affected.

In the existing technologies, chemical reagents or other special processes are also used to treat the gliadin, as to improve its dispersibility and stability. For example, patent document CN108938598A discloses a method for modifying a corn gliadin using a succinic anhydride. This method maintains pH of solution to be alkaline in the process of a reaction, and drug loaded particles obtained by the reaction are good in dispersibility, narrow in particle size distribution, and uniform in size. However, this technology introduces a succinyl group into an original protein molecule, to obtain succinylated corn gliadin particles. Although the introduction of the succinic acid group enhances interaction between hydrophobic drug molecules and a protein carrier, it weakens the functions of the gliadin particles, and the succinic anhydride introduced is a Class-3 carcinogen, the safety of the product is greatly reduced. Patent document CN114699333A discloses an anti-pollution skincare composition and a preparation method and application thereof. It uses a low-temperature plasma process to treat corn gliadin nanoparticles, and the stability and ultraviolet absorption intensity of the corn gliadin nanoparticles are significantly improved. However, the cost of the low-temperature plasma process is relatively high and the process conditions are not easy to control.

At present, how to achieve uniform dispersion of the gliadin in water by simple and controllable process treatment without the use of other high-molecular materials or toxic chemical reagents; and maintain the uniform dispersion in the water still under the high-temperature thermal sterilization treatment, long-term storage, or presence of the sodium chloride is an urgent technical problem to be solved.

SUMMARY

In order to solve the above technical problem, the present invention provides a method for modifying a gliadin and an application thereof. It uses a specific proline endoprotease as a modifying agent, and modifies the gliadin by gradient-adjusting the pH value of solution in the process of an enzymatic hydrolysis reaction. A modified gliadin obtained may still maintain a uniform dispersion state in water after high-temperature thermal sterilization or long-term storage, or in the presence of sodium chloride.

The present invention provides a method for modifying a gliadin, characterized in that the method comprises the following steps: dissolving the gliadin in a solvent to obtain gliadin solution; and adding a proline endoprotease to the gliadin solution for a reaction, and adjusting the pH value of solution to neutral according to a gradient, to obtain a modified gliadin.

Further, the step of adjusting the pH value of the solution according to the gradient refers to adjusting the pH value of the solution to 5.0±0.2 (such as 4.8, 4.9, 5.0, 5.1, 5.2 specifically) after adding the proline endoprotease to treat for 0.5-2 h (such as 0.5, 1, 1.5, 2 h specifically), adjusting the pH value of the solution to 6.0±0.2 (such as 5.8, 5.9, 6.0, 6.1, 6.2 specifically) after continuing to react for 0.5-2 h (such as 0.5, 1, 1.5, 2 h specifically), adjusting the pH value of the solution to 7.0±0.2 (such as 6.8, 6.9, 7.0, 7.1, 7.2 specifically) after continuing to react for 0.5-2 h, and continuing to react for 0.5-2 h (such as 0.5, 1, 1.5, 2 h specifically).

Further, the step of adjusting the pH value of the solution according to the gradient refers to adjusting the pH value of the solution to 5.0 after adding the proline endoprotease to treat for 1 h, adjusting the pH value of the solution to 6.0 after continuing to react for 1 h, adjusting the pH value of the solution to 7.0 after continuing to react for 1 h, and continuing to react for 1 h.

Further, the solvent is selected from one or more of ethanol aqueous solution, isopropanol aqueous solution, n-butanol aqueous solution, butanediol aqueous solution, glycerol aqueous solution, or ethylene glycol aqueous solution. Preferably the solvent is ethanol aqueous solution, more preferably 20-80% of the ethanol aqueous solution (such as 20, 30, 40, 50, 60, 70, and 80% specifically), and further preferably 70% of the ethanol aqueous solution.

Further, the gliadin is selected from one or more of corn gliadin, wheat gliadin, barley gliadin, oat gliadin, and rice gliadin. Preferably the gliadin is corn gliadin.

Further, the mass concentration of the gliadin solution is 5-25 mg/mL, such as 5, 6, 7, 8, 9, 10, 11, 12, 13, 14, 15, 16, 17, 18, 19, 20, 21, 22, 23, 24, and 25 mg/mL specifically.

Further, the mass concentration of the proline endoprotease is 0.5-2.5 mg/mL, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mg/mL specifically.

Further, the volume ratio of the proline endoprotease to the gliadin solution is 1:5-15, such as 1:5, 1:6, 1:7, 1:8, 1:9, 1:10, 1:11, 1:12, 1:13, 1:14, 1:15 specifically, preferably 1:10.

Further, the temperature of the reaction is 35-45° C., such as 35, 36, 37, 38, 39, 40, 41, 42, 43, 44, 45c, preferably 40° C.

In some embodiments of the present invention, the method includes the following steps: at a room temperature, a corn gliadin is dissolved in 70% of the ethanol aqueous solution, the above solution is added to water, and mixed uniformly, the temperature is raised to 50° C. after it is rotary-evaporated at 40° C. for 10 min, sample solution is collected after a part of liquid is evaporated, water is added to a constant volume, and mixed uniformly, to obtain corn gliadin solution. The corn gliadin solution is taken and placed stilly in a 40° C. water bath for 5 min, a proline endoprotease is added to the corn gliadin solution in a volume ratio of 1:10, it is reacted under the conditions of the 40° C. water bath, the pH value is adjusted to 5.0 after the proline endoprotease is added to treat for 1 h, the pH value is adjusted to 6.0 after it is reacted for 1 h, finally the pH value is adjusted to 7.0 after it is continued to react for 1 h, and the reaction is terminated after it is continued to react for 1 h, to obtain a modified corn gliadin.

The present invention further provides a modified gliadin prepared by the method as above.

The present invention further provides a product comprising the modified gliadin as above.

Further, the product comprises a modified gliadin carrier and its loaded functional components.

The present invention further provides an application of the modified gliadin or the product in preparation of foods, drugs, health products, cosmetics, feeds, and coatings.

The beneficial effects of the present invention are as follows.

The modified gliadin obtained by the present invention may be uniformly dispersed in water, and may still maintain a uniform dispersion state in the water after high-temperature thermal sterilization and long-term storage, or even in the presence of sodium chloride, it has good thermal stability, salt resistance, and storage stability.

DETAILED DESCRIPTION OF THE EMBODIMENTS

Figure 1:
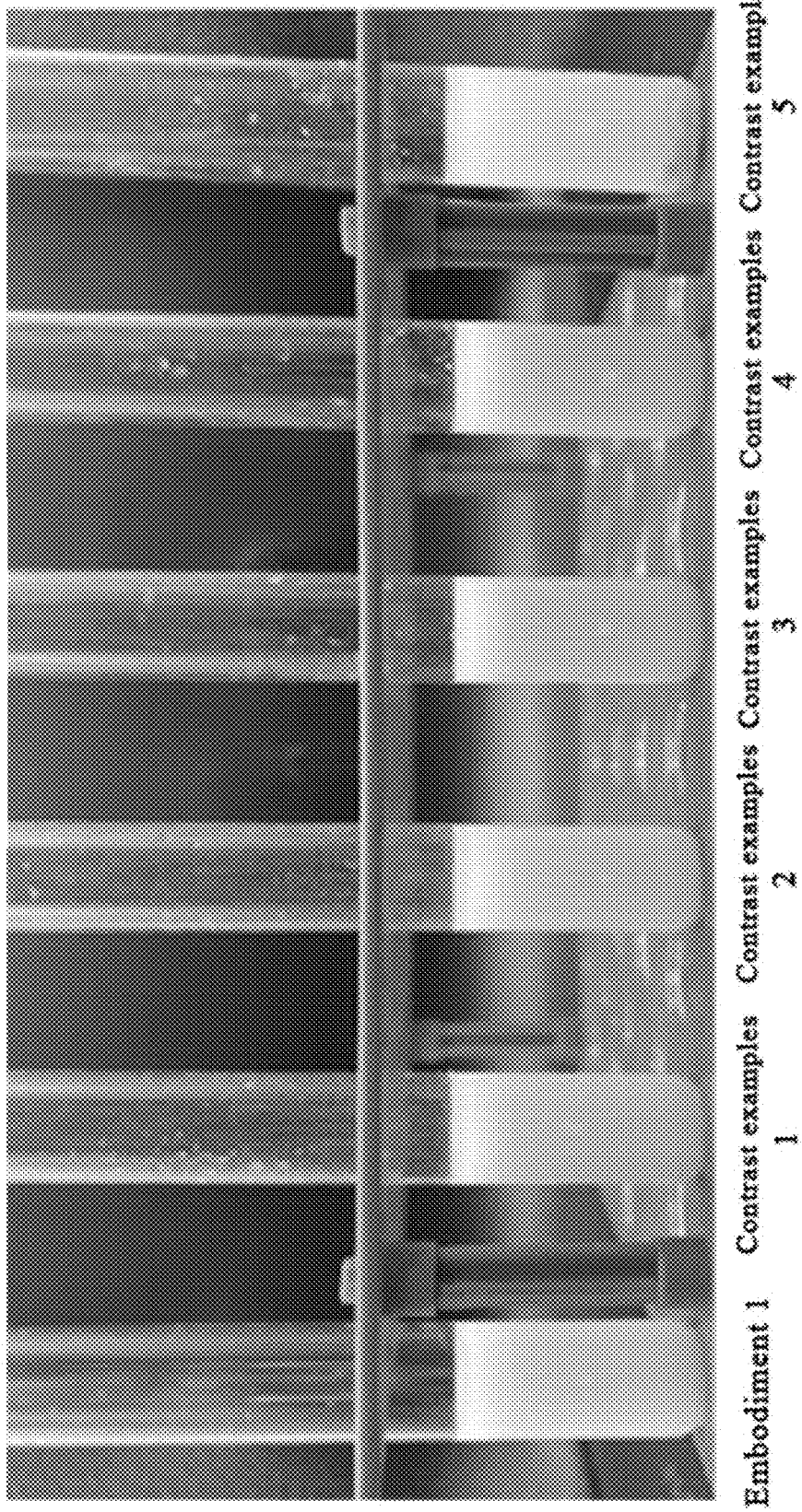
FIG. 1 shows a comparison diagram of a thermal stability condition before thermal treatment.

Unless otherwise defined, all scientific and technical terms used in the present invention have the same meaning as would normally be understood by a person skilled in the technical field to which the invention relates.

The following embodiments of the invention are described in detail in conjunction with embodiments, but those skilled in the art will understand that the following embodiments are used only to illustrate the invention and should not be regarded as limiting the scope of the invention. Where the specific conditions are not indicated in the embodiment, they shall be carried out in accordance with the usual conditions or those recommended by the manufacturer. The reagents or instruments used, where the manufacturer is not indicated, are conventional products that can be obtained through market purchase.

Embodiment 1

3 g of a corn gliadin is weighed and added to 50 mL of 70% ethanol aqueous solution under the condition of a room temperature, and after being magnetic-stirred until complete dissolution, it is slowly injected into 150 mL of magnetic-stirred ultrapure water by using an injector, and it is continuously stirred for 1 min to ensure uniform mixing of solution before rotary evaporation treatment is performed. After being rotary-evaporated at 40° C. for 10 min, the temperature is raised to 50° C., a sample is collected after 50 mL of liquid is evaporated, pure water is added to a constant volume of 200 mL, and it is stirred uniformly, to obtain corn gliadin solution.

20 mL of the corn gliadin solution is taken and placed stilly in a 40° C. water bath for 5 min, so that the interior reaches an appropriate reaction temperature for an enzyme. The enzyme is added in a ratio of proline endoprotease:corn gliadin solution=1:10 (v/v), it is magnetic-stirred and reacted under the condition of the 40° C. water bath. The pH value is adjusted to 5.0 after the proline endoprotease is added to treat for 1 h, the pH value is adjusted to 6.0 after it is reacted for 1 h, finally the pH value is adjusted to 7.0 after it is continued to react for 1 h, and the reaction is terminated after it is continued to react for 1 h, to obtain a modified corn gliadin. The modified corn gliadin is stored at a room temperature.

Contrast Example 1

This contrast example uses the method of Embodiment 1 to prepare corn gliadin solution. 20 mL of the corn gliadin solution is taken and placed stilly in a 40° C. water bath for 5 min, so that the interior reaches an appropriate reaction temperature for an enzyme. The enzyme is added in a ratio of proline endoprotease:corn gliadin solution=1:10 (v/v), it is magnetic-stirred and reacted under the condition of the 40° C. water bath. Its pH value is not adjusted, and the reaction is terminated after the reaction is performed for 4 h, to obtain a modified corn gliadin. The modified corn gliadin is stored at a room temperature.

Contrast Example 2

This contrast example uses the method of Embodiment 1 to prepare corn gliadin solution. 20 mL of the corn gliadin solution is taken and placed stilly in a 40° C. water bath for 5 min, so that the interior reaches an appropriate reaction temperature for an enzyme. The enzyme is added in a ratio of proline endoprotease:corn gliadin solution=1:10 (v/v), it is magnetic-stirred and reacted under the condition of the 40° C. water bath. The pH value of solution is adjusted to 5.0 after 1 h of the reaction, and then a thermal insulation reaction is performed only without adjusting its pH value. The reaction is terminated after it is continued to react for 3 h, to obtain a modified corn gliadin. The modified corn gliadin is stored at a room temperature.

Contrast Example 3

This contrast example uses the method of Embodiment 1 to prepare corn gliadin solution. 20 mL of the corn gliadin solution is taken and placed stilly in a 40° C. water bath for 5 min, so that the interior reaches an appropriate reaction temperature for an enzyme. The enzyme is added in a ratio of proline endoprotease:corn gliadin solution=1:10 (v/v), it is magnetic-stirred and reacted under the condition of the 40° C. water bath. The pH value of solution is adjusted to 6.0 after 1 h of the reaction, and then a thermal insulation reaction is performed only without adjusting its pH value. The reaction is terminated after it is continued to react for 3 h, to obtain a modified corn gliadin. The modified corn gliadin is stored at a room temperature.

Contrast Example 4

This contrast example uses the method of Embodiment 1 to prepare corn gliadin solution. 20 mL of the corn gliadin solution is taken and placed stilly in a 40° C. water bath for 5 min, so that the interior reaches an appropriate reaction temperature for an enzyme. The enzyme is added in a ratio of proline endoprotease:corn gliadin solution=1:10 (v/v), it is magnetic-stirred and reacted under the condition of the 40° C. water bath. The pH value of solution is adjusted to 7.0 after 1 h of the reaction, and then a thermal insulation reaction is performed only without adjusting its pH value. The reaction is terminated after it is continued to react for 3 h, to obtain a modified corn gliadin. The modified corn gliadin is stored at a room temperature.

Contrast Example 5

This contrast example uses the method of Embodiment 1 to prepare corn gliadin solution. 20 mL of the corn gliadin solution is taken and placed stilly in a 40° C. water bath for 5 min, so that the interior reaches an appropriate reaction temperature for an enzyme. The enzyme is added in a ratio of papain:corn gliadin solution=1:10 (v/v), it is magnetic-stirred and reacted under the condition of the 40° C. water bath. The pH value is adjusted to 5.0 after the papain is added to treat for 1 h, the pH value is adjusted to 6.0 after it is reacted for 1 h, finally the pH value is adjusted to 7.0 after it is continued to react for 1 h, and the reaction is terminated after it is continued to react for 1 h, to obtain a modified corn gliadin. The modified corn gliadin is stored at a room temperature.

Embodiment 2: Performance Detection Method and Result 1.1. Determination of Thermal Stability 3 mL of each sample solution is taken and placed in a glass tube, it is placed in an 85° C. oil bath. It is heated at a constant temperature for 10 min after the center temperature of solution is raised to 85° C. A sample after thermal treatment is placed stilly under the condition of a room temperature to observe whether there are apparent changes such as layering and precipitating, and a picture is taken to record.

1.2. Determination of Salt Resistance 5 mL of sample solution before the thermal treatment is taken and placed in a test tube, 1.5 M NaCl is added, and it is placed stilly for 15 min to observe for 10 s whether the solution has a layering phenomenon, and a picture is taken to record.

1.3. Determination of Particle Size 1 mL of each sample solution before heating is taken and placed in a centrifuge tube, after being filtered with a 0.1 micron membrane, pure water is added to dilute until 10 mL, and its particle size change with reaction time is measured by a nanoscale Malvin particle size analyzer. Determination condition: the refractive indexes of protein and water are set to 1.458 and 1.333 respectively.

3 mL of each sample solution after heating is taken and placed in the centrifuge tube, and its particle size change with reaction time is measured by the nanoscale Malvin particle size analyzer. Determination condition: the refractive indexes of protein and water are set to 1.458 and 1.333 respectively, and it is measured under 1-30% of laser occlusion.

1.4. Result 1.4.1. Determination Result of Thermal Stability

As can be seen from FIG. 1, before the thermal treatment, Embodiment 1 and Contrast examples 1-4 are all uniform and stable dispersion solution, and there are no apparent phenomena such as layering and precipitating when placed stilly at the room temperature. Before the thermal treatment, flocculation and precipitation occur already in Contrast example 5 after pH is adjusted.

Figure 2:
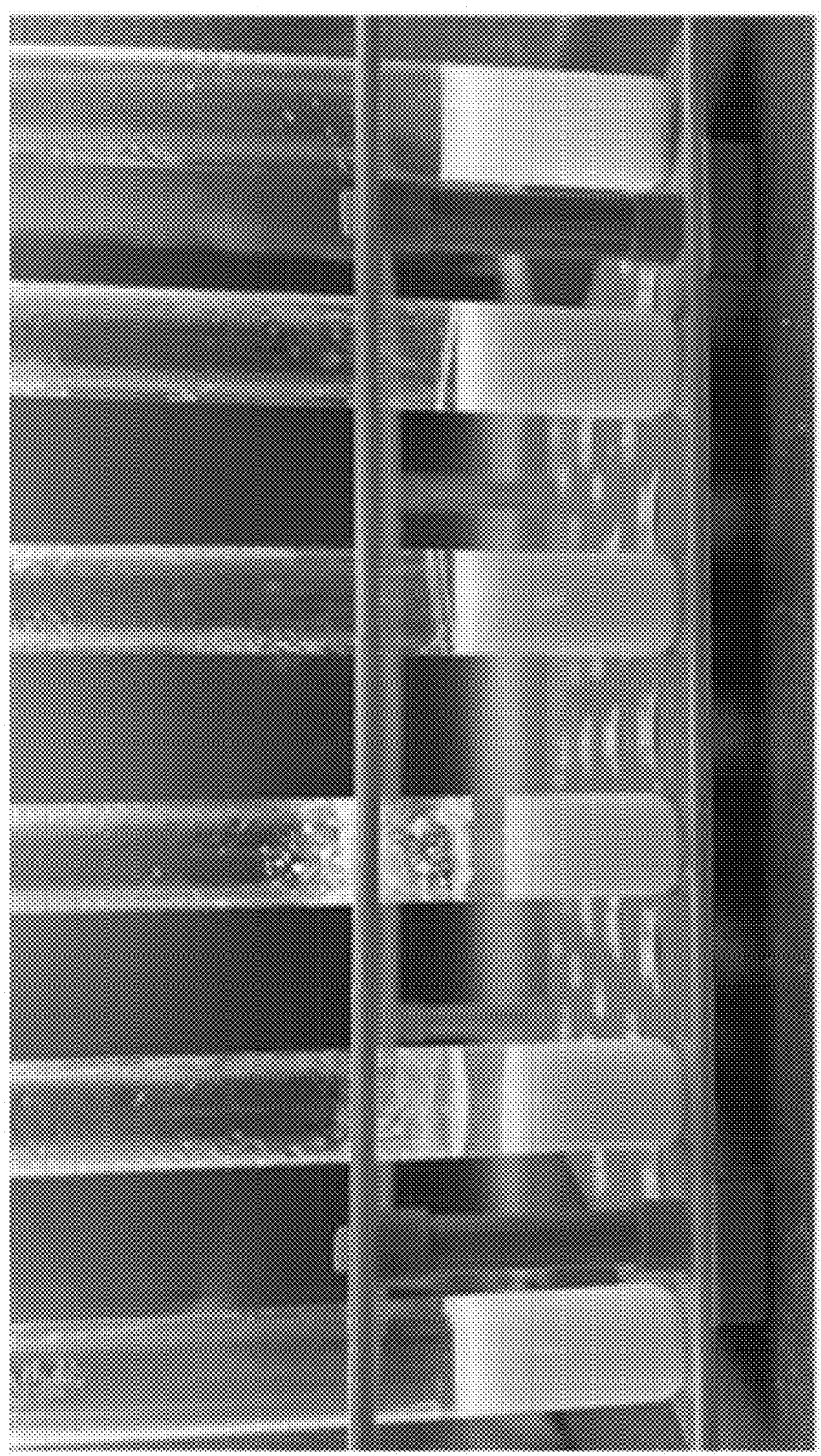
FIG. 2 shows a comparison diagram of a thermal stability condition after thermal treatment.

As can be seen from FIG. 2, after the thermal treatment, Embodiment 1 still maintains a uniform and stable dispersion state, there is no apparent layering and there is no precipitating phenomenon at the bottom; the apparent layering occurs in Contrast example 1, all protein particles are precipitated at the bottom of the test tube, thus the thermal stability is the worst; there is no apparent layering in Contrast example 2, but the test tube is shaken, it may be found that a large number of protein aggregation particles with the larger size are attached to a tube wall, and it may be observed with naked eyes; there is no apparent layering in Contrast examples 3 and 4, but slight precipitating occurs at the bottom after being placed stilly. By comparison, it may be seen that Embodiment 1 has the highest thermal stability, it is significantly superior to Contrast examples 1-4; and the flocculation and precipitation occur in Contrast example 5.

From Table 1, it may be seen that before the thermal treatment, Embodiment 1 and Contrast examples 3 and 4 all have the smaller particle sizes than Contrast examples 1 and 2. It is indicated from experimental results that compared to not adjusting pH or adjusting pH to acidity, the treatment of gradient-adjusting pH or adjusting pH to weak acidity or neutral is more helpful to the enzymatic hydrolysis of the corn gliadin by the proline endoprotease. After the thermal treatment, the increase ranges in particle size of Embodiment 1 and Contrast examples 3 and 4 are all smaller than those of Contrast examples 1 and 2. It is indicated from experimental results that compared to not adjusting pH or adjusting pH to acidity, the thermal stability of the corn gliadin after the treatment of gradient-adjusting pH or adjusting pH to weak acidity or neutral is relatively high.

After the thermal treatment, the increase range in particle size of Embodiment 1 is far smaller than that of Contrast example 5. It is indicated from experimental results that compared with a papain, the thermal stability of the corn gliadin treated with the proline endoprotease is significantly higher.

TABLE 1

Determination results of particle sizes before and after thermal treatment

| | Before thermal treatment/min | | After thermal treatment/min | | |
|---|---|---|---|---|---|
| | Average value | Standard deviation | Average value | Standard deviation | Particle size increase/% |
| Embodiment 1 | 218.40 | 5.85 | 3.55 | 0.29 | 1525.46% |
| Contrast examples 1 | 794.90 | 65.19 | 12.67 | 0.65 | 1493.91% |
| Contrast examples 2 | 1278.67 | 56.89 | 164.33 | 2.52 | 12751.63% |
| Contrast examples 3 | 142.30 | 2.69 | 0.32 | 0.01 | 124.88% |
| Contrast examples 4 | 132.20 | 0.60 | 0.44 | 0.07 | 232.83% |
| Contrast examples 5 | 12.41 | 1.57 | 15.31 | 1.78 | 123268.25% |

1.4.2. Determination Result of Salt Resistance

Figure 3:
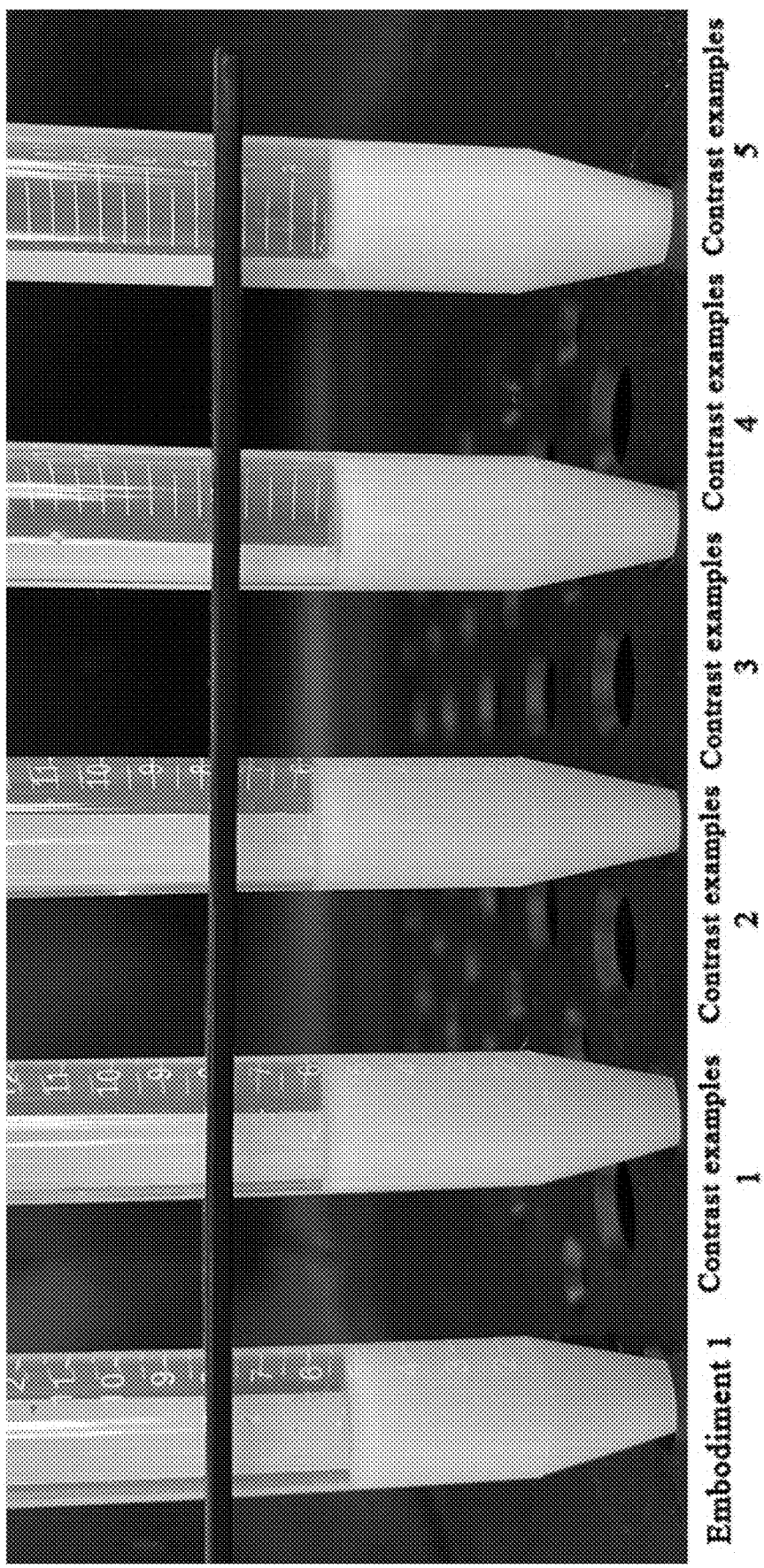
FIG. 3 shows a comparison diagram of a salt resistance condition before NaCl treatment.

As can be seen from FIG. 3, before treatment, Embodiment 1 and Contrast examples 1-4 are all uniform and stable dispersion solution, and there are no apparent phenomena such as layering and precipitating when placed stilly at the room temperature.

Figure 4:
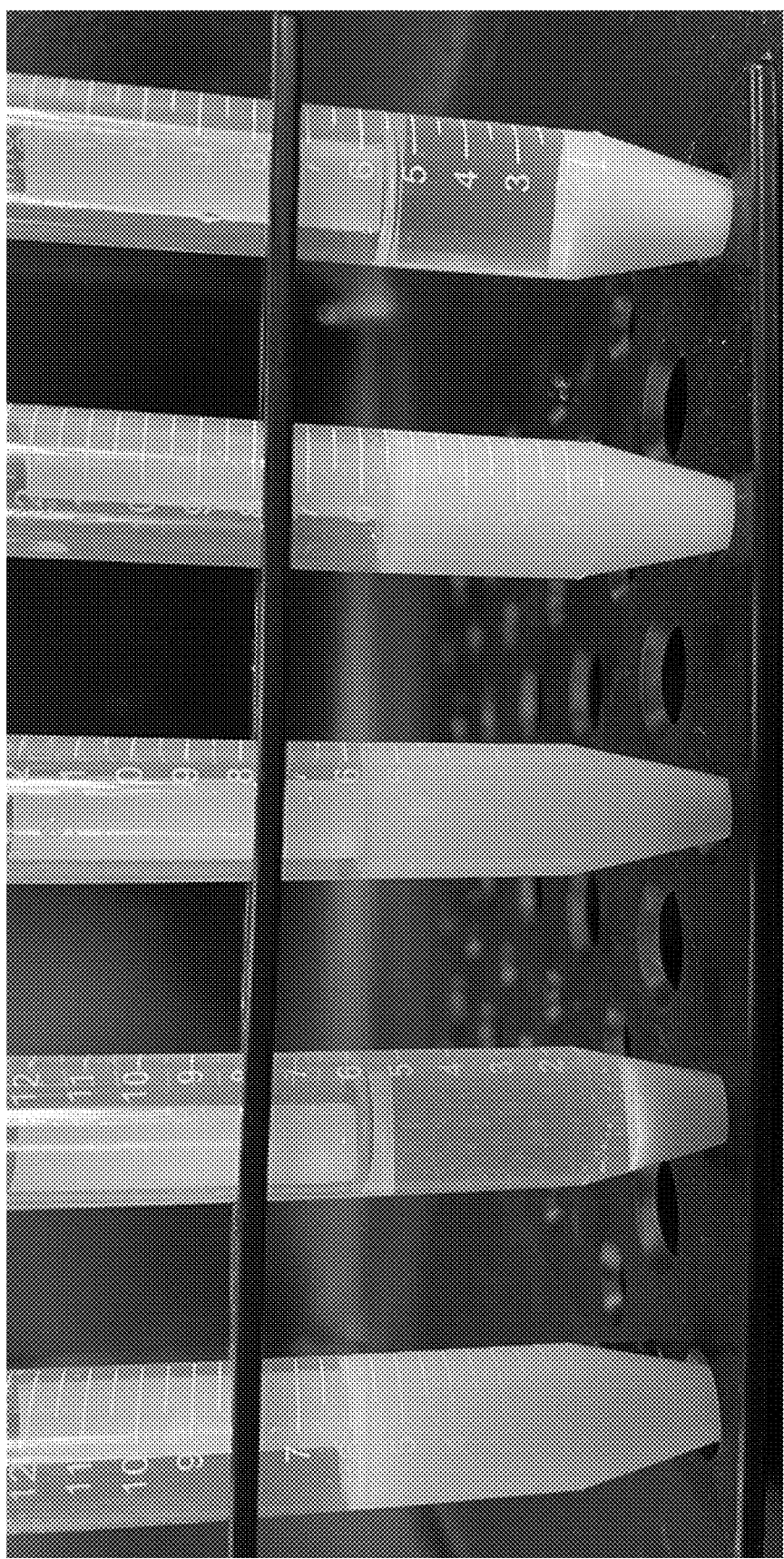
FIG. 4 shows a comparison diagram of a salt resistance condition after NaCl treatment.

As can be seen from FIG. 4, after 1.5 M NaCl is added, Embodiment 1 still maintains a uniform and stable dispersion state, there is no apparent layering and there is no precipitating phenomenon at the bottom; the apparent layering occurs in Contrast example 1, and all protein particles are precipitated at the bottom of the test tube; slight layering occurs in Contrast example 2, and a part of protein particles are precipitated at the bottom of the test tube; there is no apparent layering phenomenon in Contrast example 3, and slight precipitating occurs at the bottom after being placed stilly; the apparent layering also occurs in Contrast example 4, and all protein particles are precipitated at the bottom of the test tube; and the flocculation and precipitation occur in Contrast example 5. By comparison, it may be seen that Embodiment 1 has the highest salt resistance and is significantly superior to Contrast examples 1-4.

It is indicated from the above results that the modification effect of the proline endoprotease is significant after pH gradient adjustment. The modified gliadin obtained by the present invention may be uniformly dispersed in water, and may still maintain a uniform dispersion state in the water after high-temperature thermal sterilization and long-term storage, or even in the presence of sodium chloride, it has good thermal stability, salt resistance, and storage stability.

Finally, it should be noted that the above embodiments are only used to illustrate the technical scheme of the invention, and not to restrict it; Notwithstanding the detailed description of the invention by reference to the foregoing embodiments, it should be understood by persons of ordinary skill in the art that the technical scheme recorded in the foregoing embodiments may still be modified or equivalent to some or all of the technical features thereof; Such modification or replacement shall not remove the essence of the corresponding technical scheme from the scope of the technical scheme of each embodiment of the invention.

What is claimed is:

1. A method for modifying a gliadin, comprising the following steps:
    completely dissolving gliadin in a solvent with stirring to obtain a first gliadin solution;
    adding the first gliadin solution to ultrapure water then stirring to provide a uniformly mixed gliadin solution;
    evaporating liquid from the uniformly mixed gliadin solution and adding pure water to a predetermined volume to obtain a second gliadin solution having a mass concentration of gliadin of 5-25 mg/mL;
    adding a proline endoprotease to the second gliadin solution at a volume ratio of 1:5-15 and to provide a mass concentration of proline endoprotease of 0.5-2.5 mg/mL to obtain a third gliadin solution for a reaction, and adjusting a pH value of the third gliadin solution during the reaction to neutral according to a gradient comprising:
        adjusting the pH value of the third gliadin solution to 5.0±0.2 after adding the proline endoprotease then reacting for 1-1.5 h, then
        adjusting the pH value of the third gliadin solution to 6.0±0.2 then continuing to react for 1-1.5 h, then
        adjusting the pH value of the third gliadin solution to 7.0±0.2 and then continuing to react for 1-1.5 h; and
    thereby obtaining modified gliadin, wherein the modified gliadin has uniform and stable dispersion in water after heating to 85° C. for 10 min or after 15 minutes in a 1.5 M NaCl solution.

2. The method according to claim 1, wherein in the step of adjusting the pH value of the third gliadin solution during the reaction according to the gradient comprises:
    adjusting the pH value of the third gliadin solution to 5.0 after adding the proline endoprotease to then reacting for 1 h, then
    adjusting the pH value of the third gliadin solution to 6.0 then continuing to react for 1 h, then
    adjusting the pH value of the third gliadin solution to 7.0 and then continuing to react for 1 h.

3. The method according to claim 1, wherein the solvent is selected from one or more of ethanol aqueous solution, isopropanol aqueous solution, n-butanol aqueous solution, butanediol aqueous solution, glycerol aqueous solution, or ethylene glycol aqueous solution;
    the gliadin is selected from one or more of corn gliadin, wheat gliadin, barley gliadin, oat gliadin, and rice gliadin;
    the temperature of the reaction is 35-45° C.

4. The method according to claim 3, wherein the solvent is 20-80% by volume of the ethanol aqueous solution;
    the gliadin is the corn gliadin;
    the temperature of the reaction is 40° C.

5. The method according to claim 1, wherein the volume ratio of the proline endoprotease to the gliadin in the third gliadin solution is 1:10.

* * * * *